United States Patent [19]
Polaschegg et al.

[11] Patent Number: 5,336,194
[45] Date of Patent: Aug. 9, 1994

[54] IMPLANTABLE APPARATUS

[75] Inventors: Hans-Dietrich Polaschegg, Oberursel; Bernd Steinbach, Bad Homburg v.d.H., both of Fed. Rep. of Germany

[73] Assignee: Fresenius AG, Bad Homburg, Fed. Rep. of Germany

[21] Appl. No.: 97,673

[22] Filed: Jul. 27, 1993

[30] Foreign Application Priority Data

Aug. 1, 1992 [DE] Fed. Rep. of Germany ....... 4225524

[51] Int. Cl.$^5$ .............................................. A61M 5/32
[52] U.S. Cl. .................................. 604/175; 604/132
[58] Field of Search ............... 604/132, 891.1, 890.1, 604/131, 175

[56] References Cited
U.S. PATENT DOCUMENTS

| | | | |
|---|---|---|---|
| 3,731,681 | 5/1973 | Blackshear et al. | 128/214 F |
| 3,951,147 | 4/1976 | Tucker et al. | 128/260 |
| 4,140,122 | 2/1979 | Kühl et al. | 128/260 |
| 4,496,343 | 1/1985 | Prosl et al. | 604/86 |
| 4,772,270 | 9/1988 | Wiita et al. | 604/175 |
| 4,929,236 | 5/1990 | Sampson | 604/175 |
| 4,931,050 | 6/1990 | Idriss | 604/891.1 |
| 4,969,873 | 11/1990 | Steinbach et al. | 604/93 |
| 5,053,031 | 10/1991 | Borsanyi | 604/891.1 |
| 5,085,656 | 2/1992 | Polaschegg | 604/891.1 |
| 5,108,377 | 4/1992 | Cone et al. | 604/175 |
| 5,137,529 | 8/1992 | Watson | 604/891.1 |

FOREIGN PATENT DOCUMENTS

| | | |
|---|---|---|
| 134745 | 3/1985 | European Pat. Off. . |
| 3518841 | 11/1986 | Fed. Rep. of Germany . |
| 3639980 | 5/1988 | Fed. Rep. of Germany . |

*Primary Examiner*—John G. Weiss
*Attorney, Agent, or Firm*—Marshall, O'Toole, Gerstein, Murray & Borun

[57] ABSTRACT

Implantable infusion apparatus comprising a chamber sealed by a septum and having an outlet aperture leading therefrom, to which a catheter tube is connected. A wire anchored in the chamber base projects into the catheter lumen, forming a ring slot whose diameter is smaller than the average size of a punched out particle. The wire thus serves as a particle retention means.

4 Claims, 2 Drawing Sheets

IMPLANTABLE APPARATUS

BACKGROUND OF THE INVENTION

1. Field of the Invention

The invention concerns an implantable apparatus for dosed administration of liquid medicines into the human body, comprising a housing having at least one chamber for storing the medicine, an inlet aperture in the housing sealed by means of a perforatable septum and flow-connected with the chamber, an outflow aperture in the housing, a catheter tube joined to the outflow aperture, and a particle retention device in the area of the outflow aperture.

2. Description of Background Technology

Implantable infusion arrangements or infusion ports are known, wherein the implantation location and the administration location are separate from each other. These ports conventionally consist of a medicine reservoir implanted under the skin and comprising a housing with a perforatable septum. A catheter tube extends from an outflow aperture provided in the housing, whereby the other end of said catheter tube is connected to the administration location.

Known implantable infusion arrangements therefore differ from conventional catheters, in that there is no permanent perforation of the skin in such known arrangements. Such implantable infusion devices, with which a bolus is administered, are known from, for example, DE-PS 26 26 348 (May 31, 1979) and its counterpart U.S. Pat. No. 4,140,122 (Feb. 20, 1979), DE-OS 35 18 841 (Nov. 27, 1986) and EP 134,745 (Mar. 20, 1985).

Furthermore, implantable infusion pumps are known, having constructions corresponding substantially to that of the implantable infusion arrangements described above. These infusion pumps comprise a pumping device which evenly pumps the liquid medicine provided in the reservoir through the catheter. The reservoir chamber is usually separated by means of a gas impermeable flexible wall from a further chamber with an isobar expanding pumping means. Such infusion pumps are known from, for example, U.S. Pat. Nos. 4,496,343 (Jan. 29, 1985) and 3,731,681 (May 8, 1973), DE-PS 26 04 113 (Mar. 25, 1982) and its counterpart U.S. Pat. No. 3,951,147 (Apr. 20, 1976), DE-PS 39 15 251 (Feb. 11, 1993) and its counterpart U.S. Pat. No. 5,085,656 (Feb. 4, 1992) and AT-PS 1631/88 (Apr. 15, 1990) and its counterpart U.S. Pat. No. 4,969,873 (Nov. 13, 1990).

In addition to a chamber which is continuously subject to pump pressure and dispenses the stored medicine through a capillary acting as a flow-regulating medium, such infusion pumps may also comprise a further chamber having a further injection aperture sealed by a septum, whereby the chamber is also connected with the outflow aperture, but not subject to pump pressure. An apparatus of this type is known, e.g., from U.S. Pat. No. 4,496,343 and DE-PS 39 15 251.

The infusion apparatus is implanted in a predetermined location under the skin. For the purpose of infusion, a hollow needle (cannula) pierces the skin and the septum of the infusion apparatus positioned underneath the skin. Consequently, there is a danger of skin, tissue or septum particles being punched out or otherwise introduced into the cavity of the infusion port and that the outflow aperture and the catheter will become clogged by such particles. A variety of more or less expensive filter arrangements has been proposed to avoid such clogging by particles. Such filter arrangements are mentioned in the above-identified patent publications and usually consist of several parts, which must be mutually sealed. As a result, the installation of such filter arrangements is expensive. A filter arrangement is also known from the U.S. Pat. No. 5,108,377 (Apr. 28, 1992) wherein an outlet is integrated with a filter arrangement, resulting in a complicated structural member.

SUMMARY OF THE INVENTION

The invention is directed to solving the problem of providing an implantable infusion apparatus of the above-mentioned type, wherein the particle filtering problems are solved in a simple manner.

Accordingly, the invention provides an implantable infusion apparatus with a housing having at least one chamber for storing a liquid medicine, an inlet aperture in the housing sealed by a perforatable septum and flow-connected to the chamber, and an outlet aperture in the housing having a catheter tube with a lumen and connected to the outlet aperture with particle retention means disposed in the area of the outlet aperture. The particle retention means is a wire-shaped member or a capillary anchored in the chamber wall and projecting into said outlet aperture forming a ring slot in order to retain particles in the outlet aperture by restricting the diameter thereof.

DESCRIPTION OF THE INVENTION

From the interior of the implantable apparatus a wire or a capillary is advantageously inserted as a constricting men, her into the outflow aperture, thereby forming a ring slot, whereby the wire or capillary is anchored in the chamber wall or the chamber base. The outflow aperture is thereby formed in the conventional manner by the lumen of the catheter tube itself, which is rigidly disposed in the outflow aperture provided inside the housing. The wire or capillary thus projects into the lumen of the catheter tube and forms a ring slot between the inner wall of the catheter and the outer circumference of the wire or capillary. The annular space thereby created is so dimensioned that it safely holds back the particles which usually have an average size of less than 0.6 mm.

In such an infusion apparatus, wherein a liquid medicine reservoir is connected with a pumping arrangement which exerts constant pressure on the reservoir, a capillary, as mentioned above, serves as a flow regulator. Consequently, the diameter of the capillary, in conjunction with the viscosity of the medicine, determines the flow velocity of liquid through the capillary. According to a preferred embodiment, such a capillary is directly introduced into the lumen of the catheter tube through the wall of the medicine reservoir and a second injection chamber.

As noted above, the diameter of the ring slot is smaller than the diameter of a particle which could be sucked into the otherwise open catheter and clog it.

It is not an essential feature of the invention that the wire be disposed in the center of the catheter lumen. It may also be laterally offset from the center or float in the lumen.

According to a further embodiment, the inlet area may be fitted with an insert which is anchored directly in the inner wall of the tube or catheter by means of claws. This insert consists essentially of a star-shaped anchor member having a cylindrical core portion from which several such claws radially outwardly extend. During use, the claws cling to the inner wall of the outlet aperture or to the inner wall of the lumen of the catheter tube. The cylindrical core portion substantially corresponds to the wire-shaped insert of the first embodiment described above. To this extent, the dimensions of the cylindrical insert and those of the ring slot formed between the insert and the catheter tube are substantially identical.

Further embodiments, details and features of the invention are described by means of two examples with reference to the drawings.

DETAILED DESCRIPTION OF PREFERRED EMBODIMENTS

Figure 1:
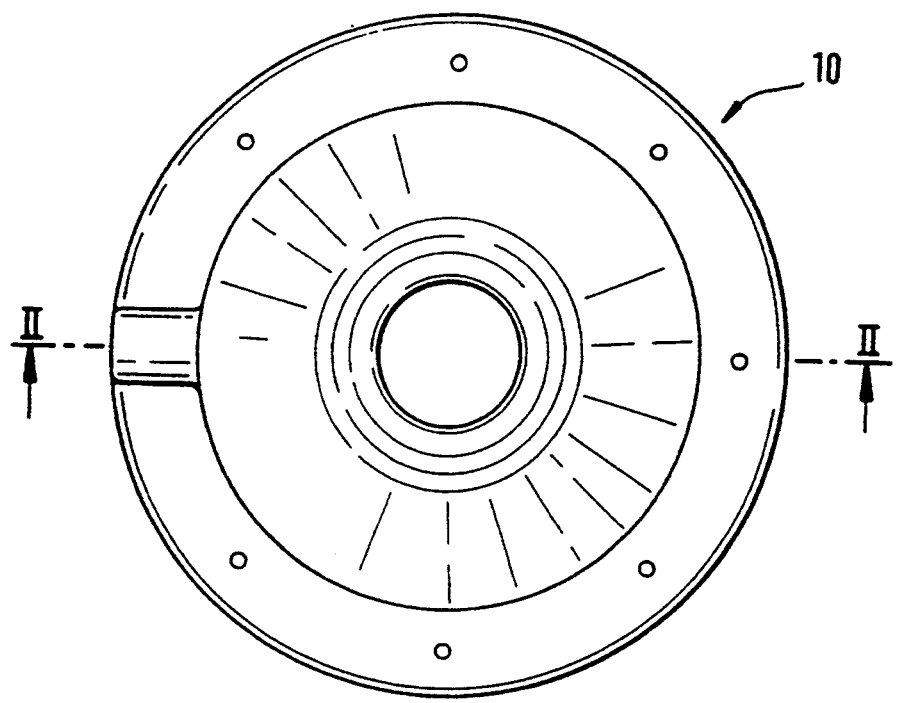
FIG. 1 is a plan view of a first embodiment of an infusion apparatus according to the invention.
Figure 2:
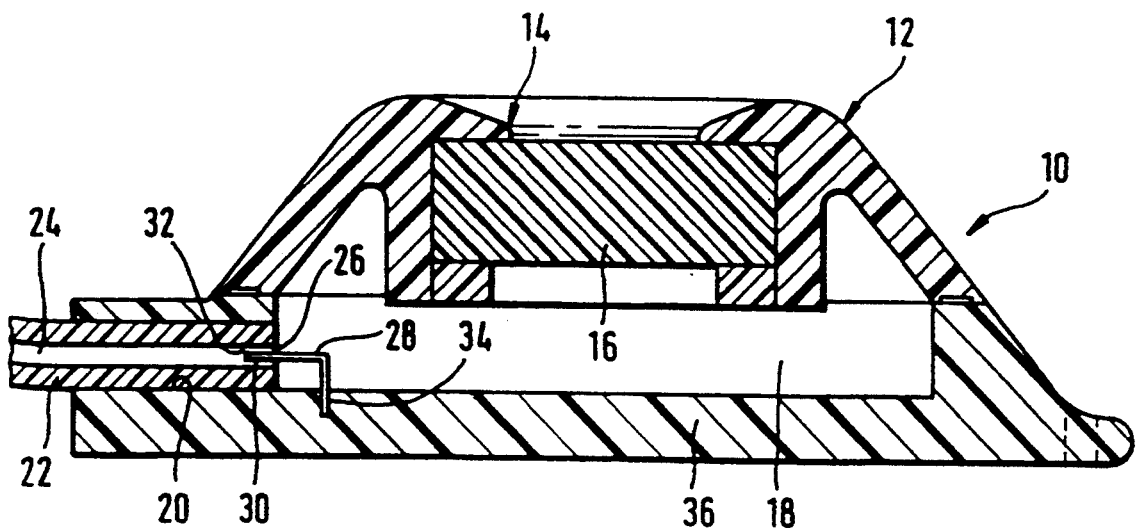
FIG. 2 shows a section along the line II—II through the embodiment shown in FIG. 1.

In FIGS. 1 and 2 an infusion apparatus generally designated 10 substantially comprises a capsule-shaped housing 12 having an inlet aperture 14 sealed by a perforatable septum 16. The housing itself comprises a chamber 18 in which a liquid medicine may be stored. An outflow aperture 20, into which a catheter tube 22 having a lumen 24 is normally inserted, extends from the chamber 18. Infusion arrangements of this type are known and described, e.g., in the above-identified patent publications, in particular EP 134,745, the disclosure of which is incorporated by reference herein. One end 30 of a wire 28 is introduced in an inlet area 26 of the lumen 24, so that a ring slot 32 is formed between the outer circumference of the wire 28 and the inner wall of the catheter tube 22 which defines the lumen 24. The thickness of the ring slot 32 ranges between 50 and 250 μ.

Another end 34 of the wire 28 is anchored in a chamber base 36, so as to determine the arrangement of the wire 28 in the inlet area 26 of the catheter tube 22.

The chamber 12, the septum 16, and the catheter tube 22 are made of conventional medically safe synthetic materials. The accuracy of manufacture of the catheter tube 22 is limited by its lumen 24, so that only lumina with a diameter of greater than 0.2 mm and a tolerance of 10% can be produced. A wire, on the other hand, can be drawn very precisely and therefore has better manufacturing tolerance.

The dimensions of the lumen 24 and the wire 28 can thus be relatively well adapted to each other. The wire 28 can therefore additionally also act as a flow regulating means. This feature, however, is not essential to the invention. The function of the wire 28 in the relatively large catheter lumen 24 is thus substantially the filtering effect, i.e. the retention of relatively large particles which may be introduced into the chamber 18, when the skin and the septum 16 are pierced with a cannula. Due to the disposition of the wire 28 in and in front of the inlet area 26 of the lumen 24 of the outflow aperture 20, such particles can no longer clog the apertures or enter them and through them invade the body of the patient.

Figure 3:
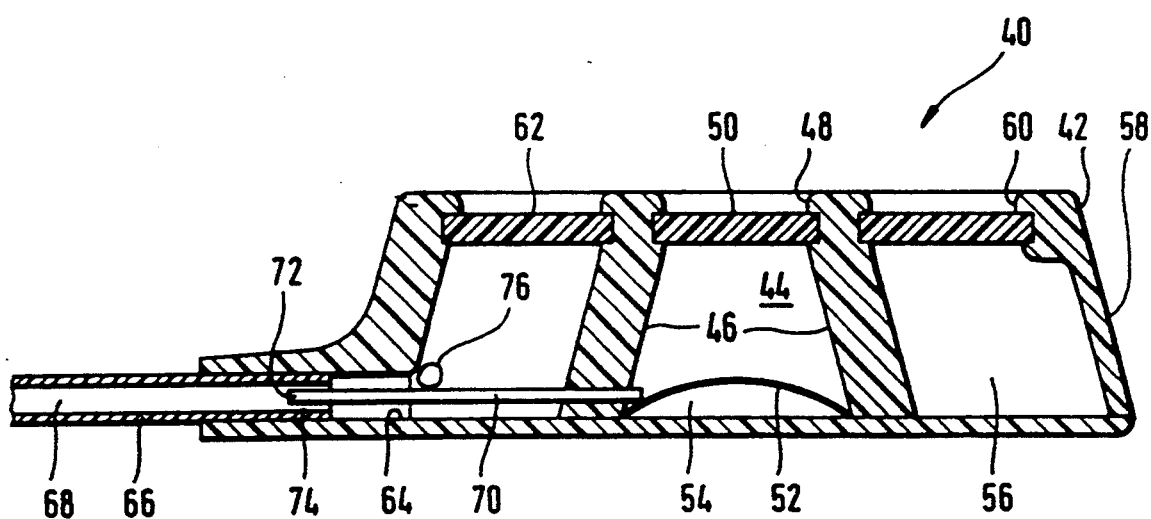
FIG. 3 shows a longitudinal section through a second embodiment of an infusion apparatus of the invention.

FIG. 3 shows an infusion pump generally designated 40 which differs from the infusion arrangement 10 shown in FIGS. 1 and 2 in that it comprises a pressure-generating chamber.

The implantable infusion pump 40 comprises a housing 42 having a first chamber 44 defined by lateral walls 46 which are of substantially hollow cylindrical form. The first chamber 44 comprises a first inlet aperture 48 sealed by a first septum 50.

The first chamber 44 is separated by a mobile gas-impermeable membrane 52 from a pumping chamber 54, in which an isobar expanding gaseous or liquid pumping agent, usually a fluoro hydrocarbon, is provided. A second annular chamber (56) defined by a substantially cylindrical outer wall 58 of the housing is provided around the substantially cylindrical lateral walls 46. The chamber 56 has an annular inlet aperture 60 sealed by a second annular septum 62.

An outlet aperture 64 extends outwardly from the second chamber 56 through the outer wall 58 of the housing 42. A catheter tube 66 with a lumen 68 is tightly inserted in the outlet aperture 64.

Consequently, the second chamber 56 is directly flow-connected to the administration location in the patient via the lumen 68. On the other hand, the first chamber 44 is directly flow-connected to the lumen 68 via a capillary tube 70 which penetrates the lateral wall 46. As shown in FIG. 3, the capillary 70, which serves as a flow limiter, passes through the annular second chamber 56, and the area of the outlet aperture 64 not occupied by the catheter tube 66, while its end 72 is inserted by a predetermined length into the lumen 68 of the catheter tube 66. The outer diameter of the capillary 70 and the diameter of the lumen 68 are thus comparable to the dimensions of the wire 28 and the lumen 24 according to the first embodiment of FIGS. 1 and 2.

It is also sufficient if the wire 28 or the capillary 70 is only inserted in the outlet aperture 20 or 64, respectively, provided that the above-specified dimensions of the ring slot formed thereby are achieved.

The infusion pump shown in FIG. 3 thus comprises two separately chargeable medicine reservoirs 44 and 56. From the first reservoir, i.e. the first chamber 44, a medicine is continuously emitted via the capillary 70 directly into the catheter 66, by the operation of the pumping device provided in the pump chamber 54. If a bolus of a second medicine is to be administered, said bolus is injected through the septum with a needle, whereby the particles to be restrained according to the invention may cause problems. In this case, as a result of the ring slot 74 defined between the capillary 70 and the catheter tube 66 with respect to the inlet aperture 64, the capillary 70 prevents introduction of the punched out particles, as exemplified by a particle 76, into the catheter tube 66. In this embodiment the essence of the invention consists in the insertion of the capillary 70 into the outlet aperture 64 of the lumen 68 of the catheter tube. Reference is additionally made to the disclosure according to the DE-PS 39 15 251 and U.S. Pat. No. 5,085,656, the respective disclosures of which are incorporated by reference.

We claim:

1. Implantable apparatus for dosed administration of liquid medicines in the human body, with a housing having at least one chamber for storing a liquid medicine defined by at least one wall, an inlet aperture in the housing sealed by a perfortable spectum and flow-connected to said chamber, and an outlet aperture in the housing connected to a catheter tube with a lumen and with particle retention means disposed in the area of the outlet aperture, wherein said particle retention means comprises a wire anchored in the chamber wall and projecting into said outlet aperture to form a ring slot in order to restrict the diameter of said outlet aperture.

2. Apparatus according to claim 1 wherein the diameter of the ring is smaller than the average diameter of a particle.

3. Implantable apparatus for dosed administration of liquid medicines in the human body, with a housing having at least one chamber for storing a liquid medicine defined by at least one wall, an inlet aperture in the housing sealed by a perfortable spectum and flow connected to said chamber, and an outlet aperture in the housing connected to a catheter tube with a lumen and with particle retention means disposed in the area of the outlet aperture, wherein said particle retention means comprises a capillary anchored in the chamber wall and projecting into said outlet aperture to form a ring slot in order to restrict the diameter of said outlet aperture.

4. Apparatus according to claim 3 wherein the diameter of the ring slot is smaller than the average diameter of a particle.

* * * * *